United States Patent
Hintermaier et al.

(10) Patent No.: US 6,527,848 B2
(45) Date of Patent: Mar. 4, 2003

(54) COMPLEX OF AN ELEMENT OF TRANSITION GROUP IV OR V FOR FORMING AN IMPROVED PRECURSOR COMBINATION

(75) Inventors: Frank Hintermaier, München (DE); Ralf Metzger, München (DE); Christoph Werner, Moosach (AT)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 09/867,291

(22) Filed: May 29, 2001

(65) Prior Publication Data

US 2002/0000175 A1 Jan. 3, 2002

Related U.S. Application Data

(63) Continuation of application No. PCT/DE99/03495, filed on Nov. 2, 1999.

(30) Foreign Application Priority Data

Nov. 26, 1998 (DE) .......................... 198 54 640

(51) Int. Cl.[7] ................................. C09K 3/00
(52) U.S. Cl. ................. 106/287.18; 427/255.32
(58) Field of Search ................. 106/287.18; 427/255.32

(56) References Cited

U.S. PATENT DOCUMENTS 5,820,664 A    10/1998  Gardiner et al.
5,916,359 A  *  6/1999  Baum et al. ............ 106/287.18
6,133,051 A  * 10/2000  Hintermaier et al. ......... 438/3
6,214,105 B1 *  4/2001  Hintermaier et al. .. 106/287.19
6,303,391 B1 * 10/2001  Hintermaier et al. ......... 438/3

FOREIGN PATENT DOCUMENTS

WO    WO 95/26355    10/1995

OTHER PUBLICATIONS

Kapoor, R. N. et al.: "Organic Compounds of Niobium and Tantalum. Reactions of Niobium and Tantalum Pentaethoxides with Dibenzoylmethane", Bulletin of the Chemical Society of Japan, vol. 40,(1967), No month provided pp. 1384–1386, Chemical Abstracts XP–002131326.

Narula, A.K. et al.: "Preparation and characterization of tantalum(V) β–diketonates", Chemical Abstracts XP–002131328 No date provided.

Itsuki, Atsushi et al.: "Tantalum compound for vapor deposition", Chemical Abstracts XP–002131327 No date provided.

* cited by examiner

Primary Examiner—David Brunsman
(74) Attorney, Agent, or Firm—Laurence A. Greenberg; Werner H. Stemer; Ralph E. Locher

(57) ABSTRACT

A new complex of an element of transition group IV or V is provided for forming an improved precursor combination for use in chemical vapor deposition (CVD). This complex dispenses with an alkoxide ligand having an α proton, so that hydrolysis of the complex no longer liberates a reducing agent.

4 Claims, No Drawings

COMPLEX OF AN ELEMENT OF TRANSITION GROUP IV OR V FOR FORMING AN IMPROVED PRECURSOR COMBINATION

CROSS-REFERENCE TO RELATED APPLICATION

This application is a continuation of copending International plication No. PCT/DE99/03495, filed Nov. 2, 1999, which designated the United States.

BACKGROUND OF THE INVENTION

Field of the Invention

The invention relates to a new complex of an element of transition group IV or V for forming an improved precursor and/or precursor combination for use in chemical vapor deposition (CVD). The term "precursor combination" refers to a mixture (e.g. a metal complex or precursor and a solvent) which is vaporized at commencement of a CVD reaction.

Precursor combinations are known from U.S. Pat. No. 5,820,664. In order to effect chemical vapor deposition of, for example, $SrBi_2Ta_2O_3$ (SBT), use is made of a precursor combination including [Ta(OiPr)$_4$thd] (see column 6, line 42), in which a Ta complex with an alkoxide ligand having an α proton and thus a potential reducing agent (to form the corresponding ketone) is present.

The precursor Bi(Ph)$_3$ has been replaced by Bi(thd)$_3$ in order to obtain stable $Bi_2O_3$ deposition rates (see a presentation by F. Hintermaier et al., given at the International Symposium on Integrated Ferroelectrics, Monterey, Calif., USA, 1998). However, Bi(thd)$_3$ is easily reduced to the metal in the presence of a reducing agent. Thus, for example, hydrolysis of the precursor [Ta(OiPr)$_4$thd] liberates HOiPr which acts as a reducing agent or in a ligand exchange reaction according to the equation:

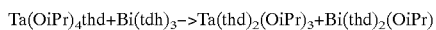
Ta(OiPr)$_4$thd+Bi(tdh)$_3$−>Ta(thd)$_2$(OiPr)$_3$+Bi(thd)$_2$(OiPr)

forms (Bi(thd)$_2$(OiPr) which undergoes an internal redox reaction with reduction of the $Bi^{3+}$ metal ion to liberate elemental bismuth.

SUMMARY OF THE INVENTION

It is accordingly an object of the invention to provide a new complex, which overcomes the hereinafore-mentioned disadvantages of the heretofore-known complexes of this general type, which is suitable as a precursor and which remains stable in chemical vapor deposition using a $Bi^{3+}$ precursor and/or, in the case of a ligand exchange reaction, promotes formation of a by-product which is thermally stable under reaction conditions of a CVD technique and in which bismuth continues to be present in oxidized form.

This object is achieved according to the invention by a complex which has only alkoxides without an α proton and very bulky ligands as complex formers.

The invention provides a complex of the formula:

M (L)$_x$(R$_3$C—O—)$_{y-x}$ where:

M is a stable central atom from transition group IV or V of the Periodic Table;

L is a β-diketonate, a β-ketiminate and/or a β-diiminate;

(R$_3$C—O—) is an alkoxide ligand in which R may be identical or different and are each an alkyl radical which has from 1 to 24 carbon atoms and may be branched or linear and substituted or unsubstituted and/or complexed;

x is not equal to zero and is from 1 to 4; and y is not equal to zero and is 2, 3, 4 or 5, depending on the oxidation state of the central atom.

The invention also provides for the use of this complex for the deposition of ferroelectric, paraelectric and high-ε layers.

Finally, the invention provides a precursor combination including the new complex as a precursor.

Preference is given to using tantalum or niobium as a central atom of the complex.

Preference is given to using the tert-butyl radical and/or the tert-pentyl radical as a tertiary radical on the alkoxide ligand.

In an advantageous embodiment, thd, namely 2,2,6,6-tetramethyl-3,5-heptanedionate, is used as a bulky ligand.

In a further advantageous embodiment, 4 alkoxide ligands and one (thd) ligand are bound to the central atom of the complex.

The term "stable central atom of the complex" refers to an element of the Periodic Table having a most abundant isotope which does not undergo radioactive decay. Preference is given to a metal selected from the group consisting of Ti, Zr, Hf, V, Nb and Ta. Particular preference is given to using Ta.

The term "alkoxide ligand" refers to the alcoholate ligand which is bound by the oxygen atom of the alcohol group and has the formula:

—O—CR$_3$ where R may be identical or different and are each an alkyl radical which has from 1 to 24 carbon atoms and may be branched or linear and substituted or unsubstituted and/or complexed. It is advantageous, for example for the alcoholate ligand to contain ether, amine and/or sulfide groups which can additionally act as donors toward the central atom.

Particular preference is given to using an alkoxide ligand of the formula:

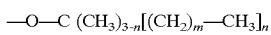
—O—C (CH$_3$)$_{3-n}$[(CH$_2$)$_m$—CH$_3$]$_n$ where:

n is in a range from 0–3; and m is in a range from 0–3.

Preference is given to using derivatives of a β-diketonate, a β-ketiminate and a β-diiminate.

2,2,6,6-tetramethyl3,5-heptanedionate is preferably used. Other preferred ligands are, for example, acetylacetonate (acac); hexafluoropentanedionate (hfac); 1,1,1-trifluoro-2,4-pentanedionate (tfac); 6,6,7,7,8,8,8-heptafluoro-2,2-dimethyl-3,5-octanedionate; 2,2,7-trimethyl-3,5-octanedionate; 1,1,1,5,5,6,6,7,7,7-decafluoro-2,4-heptanedionate; and finally 1,1,1-trifluoro-6-methyl-2,4-dionate.

The preparation of the complex is carried out through the use of a ligand exchange reaction of the type described by the following example:

A lower tantalum alkoxide, e.g. Ta(thd)$_p$(OMe)$_{5-p}$ (p can be from 1 to 4), is used as a starting material. For the preparation, this is dissolved in an alcohol, e.g. tertiary butyl or pentyl alcohol, with an addition of benzene and is refluxed while simultaneously distilling off the alcohol being liberated, in this case methanol (to shift the equilibrium in the direction of the new complex).

The complex Ta(thd) (OtBu)$_4$ as a precursor has the advantage that in the case of a reaction with Bi(thd)$_3$ it reacts to form the thermally stable compound Bi(thd)$_a$(OtBu)$_b$ (where a and b can each be 1 or 2). Furthermore, any hydrolysis which may occur liberates the alcohol tBuOH which has no a proton and therefore does not act as a reducing agent.

Ta (thd) (OtBu)$_4$ has vaporization properties similar to those of Ta(thd) (OiPr)$_4$ because both compounds have similar molecular weights.

With the foregoing and other objects in view there is provided, in accordance with the invention, a precursor combination for the deposition of SBT, comprising the combination:

Sr(thd)$_2$(pmdeta) or Sr(thd)$_2$(tetraglyme);

Bi(thd)$_3$; and

Ta(thd) (OtBu)$_4$ or Ta(thd) (OtPe)$_4$.

wherein (OtBu) is tertiary butoxy and (OtPe) is tertiary pentoxy.

However, the complexes described, in particular those of tantalum, are not only useful for the deposition of SBT.

Rather, they can be used generally for the chemical vapor deposition of thin films based on metal oxide(s).

Such thin films are employed, for example, in memory technology, e.g. for dynamic random access memories (DRAMs) and ferroelectric random access memories (FeRAMs).

In this context, the use of the complexes for the deposition of tantalum pentoxide, which will be used as a dielectric in future generations of DRAMs, is also conceivable.

Other features which are considered as characteristic for the invention are set forth in the appended claims.

Although the invention is described herein as embodied in a new complex of an element of transition group IV or V for forming an improved precursor combination, it is nevertheless not intended to be limited to the details given, since various modifications and structural changes may be made therein without departing from the spirit of the invention and within the scope and range of equivalents of the claims.

The construction and method of operation of the invention, however, together with additional objects and advantages thereof will be best understood from the foregoing description of specific embodiments.

We claim:

1. A precursor combination for the deposition of SBT, comprising the compounds:

Sr(thd)$_2$(pmdeta);

Bi(thd)$_3$; and

Ta(thd) (OtBu)$_4$.

2. A precursor combination for the deposition of SBT, comprising the compounds:

Sr(thd)$_2$ (tetraglyme);

Bi(thd)$_3$; and

Ta(thd) (OtPe)$_4$.

3. A precursor combination for the deposition of SBT, comprising the compounds:

Sr(thd)$_2$(pmdeta);

Bi(thd)$_3$; and

Ta(thd) (OtPe)$_4$.

4. A precursor combination for the deposition of SBT, comprising the compounds:

Sr(thd)$_2$(tetraglyme);

Bi(thd)$_3$; and

Ta(thd) (OtBu)$_4$.

* * * * *